(12) United States Patent
Lee et al.

(10) Patent No.: US 8,067,552 B2
(45) Date of Patent: *Nov. 29, 2011

(54) METHOD FOR PREPARING A TARGET PROTEIN USING THE SHSPS

(75) Inventors: Sang Yup Lee, Daejeon (KR); Mee Jung Han, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 815 days.

This patent is subject to a terminal disclaimer.

(21) Appl. No.: 11/915,314

(22) PCT Filed: May 23, 2005

(86) PCT No.: PCT/KR2005/001500
§ 371 (c)(1),
(2), (4) Date: Nov. 22, 2007

(87) PCT Pub. No.: WO2006/126750
PCT Pub. Date: Nov. 30, 2006

(65) Prior Publication Data
US 2008/0199907 A1 Aug. 21, 2008

(51) Int. Cl.
*C07K 1/14* (2006.01)
(52) U.S. Cl. .................................................. 530/412
(58) Field of Classification Search .................. None
See application file for complete search history.

(56) References Cited

U.S. PATENT DOCUMENTS

| | | | |
|---|---|---|---|
| 5,552,301 A | 9/1996 | Baneyx et al. | |
| 7,291,325 B2 * | 11/2007 | Lee et al. | 424/93.2 |
| 2002/0111314 A1 | 8/2002 | Ginsberg et al. | |
| 2003/0092624 A1 | 5/2003 | Wang et al. | |

FOREIGN PATENT DOCUMENTS

| | | |
|---|---|---|
| JP | 2001-033449 | 2/2001 |
| JP | 2001-061487 | 3/2001 |
| JP | 2004-043447 | 2/2004 |
| JP | 2005-084048 | 3/2005 |
| WO | 2005023847 A1 | 3/2005 |

OTHER PUBLICATIONS

Kitagawa, Masanobu, et al., "*Escherichia coli* small heat shock proteins, IbpA and IbpB, protect enzymes from inactivation by heat and oxidants", "Eur. J. Biochem.", 2002, pp. 2907-2917, vol. 269.
Lee, Do Hee, et al., "Proteasome inhibitors cause induction of heat shock proteins and trehalose, which together confer thermotolerance . . . ", "Molecular and Cellular Biology", Jan. 1998, pp. 30-38, vol. 18, No. 1, Publisher: American Society for Microbiology.
Munchbach, Martin, et al., "Multiple small heat shock proteins in rhizobia", "Journal of Bacteriology", Jan. 1999, pp. 83-90, vol. 181, No. 1, Publisher: American Society for Microbiology.
Shearstone, Jeffrey R., et al., "Biochemical characterization of the small heat shock protein IbpB from *Escherichia coli*", "The Journal of Biological Chemistry", Apr. 9, 1999, pp. 9937-9945, vol. 274, No. 15, Publisher: The American Society for Biochemistry and Molecular Biology, Inc.
Su, J. et al. , "The Methods and Application About Protein Keeps Stable When It Be Extracted and Purified", "Journal of Tianjin University of Light Industry", Mar. 2002, pp. 21-24, No. 1 (Only English Abstract Provided).
Georgiou, G., et al., "Expression of correctly folded proteins in *Escherichia coli*", "Curr. Opin. Biotechnol.", 1996, pp. 190-197, vol. 7.
Goloubinoff, P, et al., "GroE heat-shock proteins promote assembly of foreign prokaryotic ribulose bisphosphate carboxylase oligomers in . . . ", "Nature", 1989, pp. 44-47, vol. 337.
Hockney, Robert C., "Recent developments in heterologous protein production in *Escherichia coli*", "TIBTECH", 1994, pp. 456-463, vol. 12.
Langer, Thomas, et al., "Successive action of DnaK, DnaJ and GroEL along the pathway of chaperone-mediated protein folding", "Nature", 1992, pp. 683-689, vol. 356.
Larossa, RA, et al., "Physiological roles of the DnaK and GroE stress proteins: catalysts of protein folding or macromolecular sponges?", "Mol. Microbiol.", 1991, pp. 529-534, vol. 5.
Makrides, SC, "Strategies for achieving high-level expression of genes in *Escherichia coli*", "Microbiol. Rev.", 1996, pp. 512-538, vol. 60.
Meerman, HJ, et al., "High-level production of proteolytically sensitive secreted proteins in *Escherichia coli* strains impaired in the . . . ", "Ann. N.Y. Acad. Sci.", 1994, pp. 292-302, vol. 721.
Murby, M., et al., "Stabilization of recombinant proteins from proteolytic degradation in *Escherichia coli* using a dual affinity fusion . . . ", "Biotechnol. Appl. Biochem.", 1991, pp. 336-346, vol. 14.
Narberhaus, F., "Alpha-crystallin-type heat shock proteins: socializing minichaperones in the context of a multichaperone network", "Microbiol. and Molec. Biol. Rev.", Mar. 2002, pp. 64-93, vol. 66, No. 1.
Obukowicz, MG, "Enhanced heterologous gene expression in novel rpoH mutants of *Escherichia coli*", "Appl. Environ. Microbiol.", 1992, pp. 1511-1523, vol. 58.
Studer, S., et al., "Chaperone activity and homo- and hetero-oligomer formation of bacterial small heat shock proteins", "J. Biol. Chem.", 2000, pp. 37212-37218, vol. 275.

* cited by examiner

*Primary Examiner* — Anand Desai

(74) *Attorney, Agent, or Firm* — Hultquist IP; Steven J. Hultquist; Kelly K. Reynolds

(57) ABSTRACT

The present invention relates to a method for separating and purifying a target protein, a method for preparing a target protein, and a method for bioconversion by a whole cell enzyme or a partially purified enzyme. According to the present invention, when the sHSPs are added in cultivation, separation and purification processes for preparing a target protein, the target protein can be obtained at high yields by preventing the loss of protein by proteases. Also, when sHSPs are added in a reaction process using a whole cell enzyme or a partially purified enzyme, the yield of bioconversion using enzyme can be increased by preventing the loss of enzyme by proteases.

4 Claims, 6 Drawing Sheets

METHOD FOR PREPARING A TARGET PROTEIN USING THE SHSPS

CROSS-REFERENCE TO RELATED APPLICATION

This application is filed under the provisions of 35 U.S.C. §371 and claims the priority of International Patent Application No. PCT/KR2005/001500 filed May 23, 2005. The disclosure of said international patent application is incorporated herein by reference, in its entirety, for all purposes.

TECHNICAL FIELD

The present invention relates to methods for separating and purifying a target protein, methods for preparing a target protein and a method for bioconversion using a whole cell enzyme or a partially purified enzyme, in which an effective amount of the sHSPs (small heat shock proteins) are added to prevent target protein degradation by proteases.

BACKGROUND ART

According to the remarkable development of recombinant DNA technology, it has become possible to produce a large amount of useful proteins in *E. coli*, yeast, fungus, plant, animal and insect cells medically and industrially, where it could be obtained at only small amounts in nature. For example, proteins, such as interferon, interleukin 2, colony-stimulating factors, growth hormone, insulin-like growth factors and human serum albumin have been successfully produced by recombinant *E. coli* (Lee, S Y, *Trends Biotechnol.*, 14:98, 1996). Particularly, technology for high cell-density culture of *E. coli* is well established whereby target proteins can be mass-produced at high productivity so that the cost of target protein production can be reduced. However, even though useful proteins are produced at a large amount by an efficient expression vector system, final yields of proteins are rapidly decreased, if a system for isolating and purifying protein is not well established. Such steps for separation and purification become much more significant when it is difficult to synthesize proteins, much time and effort are required, or the amount of protein production itself is small.

Steps for Separating and Purifying Proteins Generally Comprise as Follows:

(1) Cell extraction: cells or tissues are disrupted by glass homogenizer, mixer, polytron and sonicator, and so on, and then separated by a centrifugation; (2) Solubilization: when insoluble proteins are separated and purified, first of all, proteins should be solubilized. Various sorts of surfactants (SDS, Triton X-100, Nonidet P-40, CHAPS etc.) are used as an agent to solubilize a biological membrane protein; (3) Separation, condensation and dialysis of proteins: an ammonium sulfate precipitation by protein solubility, a molecular weight cut off method by the difference of protein molecular weight, a dialysis method by porous cellulose membrane, etc. are used before protein sample is purified; and (4) Final purification of proteins: since methods for purifying protein are various as shown in the Table 1 below, purification should be performed by combining methods according to the object of experiment and the kind of material. In general, in initial step, a method having high process capacity is selected even though separation activity is somewhat low, and as final step approaches, a method having high separation activity is used.

TABLE 1

Typical methods for purifying protein

| Method | Feature | Kind |
|---|---|---|
| Column chromatography | Separation by pressure (or flux) Separation of a bulk of protein | LPLC (low pressure liquid chromatography) HPLC (high pressure chromatography) |
| Affinity chromatography | Chromatography using affinity between a certain material (ligand) and a protein High purity and recovery rate | Affinity chromatography by antibody column Affinity chromatography of GST fusion protein by glutathione column Protein-specific affinity chromatography |
| Other chromatography | Separation by protein charge (isoelectric point), physiological activity (chemical reactivity), molecular weight, hydrophobicity | Ion-exchange chromatography Gel filtration Reverse-phase chromatography Hydrophobic chromatography |
| Electrophoresis | Separation by high resolution electrophoresis | Isoelectric focusing SDS polyacrylamide gel electrophoresis Two dimensional gel electrophoresis |

To prevent proteolysis by protease, protease inhibitor can be mixed and used. For example, 0.4~4.0 mM Petabloc SC (AEBSF; (4-(2-Aminoethyl)-benzenesulfonyl fluoride hydrochloride), 0.1~1.0 mM PMSF (phenylmethyl sulphonyl fluoride) and 5~50 mM Leupeptin are used against neutral serine proteases, 0.5~5 mM EDTA against neutral metalloproteases, 0.1~30 mM E-64 against cysteine proteases, and 1 mM Pepstain against aspartic acid proteases, are used, also a cocktail mixed with various inhibitors is generally used.

However, proteolysis can not be completely inhibited even with use of protease inhibitors. Particularly, when target proteins are separated and purified in plant extracts, or animal organs such as pancreas, stomach, liver or spleen in which various proteases are rich, or target proteins themselves are easily attacked by proteases, the loss of proteins is very severe.

Meanwhile, sHSPs are heat shock proteins (HSPs) with a low molecular weight of 12-43 kDa, which are induced by stress, such as heat shock or the overproduction of certain proteins. One or more of the sHSPs are present in all organisms from eukaryotes to prokaryotes, and the sHSPs known till now are given in the Table 2 below.

ATP-independent sHPSs perform the function of preventing protein aggregation irreversibly by binding with protein denatured under heat stress, and cooperate with ATP-dependent heat shock proteins to make denatured proteins refold correctly thereby, returning the denatured proteins to original state. For example, Kitagawa et al. have reported that IbpA and IbpB derived from *E. coli* prevent inactivation of citrate synthase by heat or oxidants (Kitagawa et al., *Eur. J. Biochem.*, 269:2907, 2002), and Lee et al. have reported that HSP18.1 derived from pea prevents aggregation of denatured proteins, such as malate dehydrogenase (MDH), glyceraldehydes-3-phosphate dehydrogenase under heat stress (Lee et al., *EMBO J.*, 16:659, 1997). Horwitz et al., have reported that α-crystallin derived from human prevents protein aggregation so as to help correct refolding of target proteins in dialysis process of denatured target proteins (Horwitz et al., *Proc. Natl. Acad. Sci. USA*, 89:10449, 1992). It was reported that sHSPs derived from *Badyrbizobium japonicum* prevent citrate synthase aggregation by heat (Studer and Narberhaus, *J. Biol. Chem.*, 275:37212, 2000). It was reported that since Pfu-sHSP purified in an organism, which is stable under heat, protects proteins of cells under heat stress (WO 01/79250 A1), it stabilized Taq-polymerase and other enzymes at high temperature during PCR. Also, Ehrnsperger et al. have reported that sHSP 25 derived from Murine stabilizes proteins or peptides which are unstable in diagnostic assay (Ehrnsperger et al., *Anal. Biochem.*, 259:218. 1998).

Such sHSPs have a conserved region in evolutionary processes and thus has been performing substantially similar functions. The present inventors have filed an application for a patent regarding composition for protecting protein degradation containing the sHSPs and a method of two-dimensional gel electrophoresis using the sHSPs (PCT/KR03/02539). However, there has not yet been any report on efficient prevention of target protein degradation by proteases in a cultivation process for preparing target proteins, a process for separating and purifying target proteins, and a reaction process using whole cell enzymes or partly purified enzymes.

TABLE 2

| The sHSPs family | |
|---|---|
| Origin | sHSPs |
| *Agrobacterium tumefaciens* str. C58 (U. Washington) | IbpA |
| *Arabidopsis thaliana* | sHSPs |
| *Bradyrbizobium japonicum* | HSPB, HSPH, HSPC, HSPF |
| *Brucella suis* 1330 | IbpA |
| *Buchnera aphidicola* plasmid pBPS1 | sHSPs |
| *Buchnera aphidicola* str. APS (*Acyrthosiphon pisum*) | IbpA |
| *Citrus tristeza* virus | sHSPs |
| *Escherichia coli* CFT073 | IbpA, IbpB |
| *Escherichia coli* K12 | IbpA, IbpB |
| *Escherichia coli* O157: H7 EDL933 | IbpA, IbpB |
| *Escherichia coli* O157: H7 | IbpA, IbpB |
| *Helicobacter pylori* 26695 | IbpB |
| Human | HSP27, α,β-crystallin |
| *Methanococcus jannaschii* | HSP16.5 |
| *Methanopyrus kandleri* AV19 | IbpA |
| Murine | HSP25 |

TABLE 2-continued

| The sHSPs family | |
|---|---|
| Origin | sHSPs |
| *Mycobacterium leprae* strain TN | sHSPs |
| *Mycobacterium tuberculosis* | HSP16.3 |
| *Pirellula* sp. | IbpB |
| *Pisum sativum* (pea) | HSP18.1 |
| *Plasmodium falciparum* 3D7 | sHSPs |
| *Pseudomonas aeruginosa* PA01 | IbpA |
| *Pseudomonas putida* KT2440 | IbpA |
| *Saccharomyces cerevisiae* | HSP26 |
| *Salmonella enterica* subsp. enterica serovar Typhi | IbpA, IbpB |
| *Salmonella typhimurium* LT2 | IbpA, IbpB |
| *Shewanella oneidensis* MR-1 | IbpA |
| *Shigella flexneri* 2a str. 2457T | IbpA, IbpB |
| *Shigella flexneri* 2a str. 301 | IbpA, IbpB |
| *Sinorhizobium meliloti* 1021 | IbpA |
| *Sinorhizobium meliloti* plasmid pSymA | IbpA |
| *Streptococcus pyogenes* | IbpA |
| *Streptomyces coelicolor* A3(2) | sHSPs |
| *Sulfolobus solfataricus* | sHSPs |
| *Synechococcus vulcanus* | HSP16 |
| *Thermoanaerobacter tengcongensis* strain MB4T | IbpA |
| *Thermoplasma acidophilum* | IbpA |
| *Yersinia pestis* KIM | sHSPs, IbpA, IbpB |
| *Yersinia pestis* strain CO92 | IbpA, IbpB |

Accordingly, the present inventors have conducted intensive studies to develop a method for preventing target protein degradation by proteases in a cultivation process for preparing target proteins, a process for separation and purification, and an enzyme reaction using a target protein as biocatalyst, and consequently, found that the loss of target proteins by proteases can be prevented when the sHSPs are used, thereby completing the present invention.

DISCLOSURE OF INVENTION

A main object of the present invention is to provide a method for separating and purifying target proteins, in which an effective amount of the sHSPs are added in a process for separation and purification where target protein degradation by proteases occurs.

Another object of the present invention is to provide a method for preparing target proteins, in which an effective amount of the sHSPs are added in a cultivation process where target protein degradation by proteases occurs.

Still another object of the present invention is to provide a method for preparing target proteins, in which recombinant microorganisms containing sHSP gene are cultured.

Still another object of the present invention is to provide a method for bioconversion using whole cell enzymes or partially purified enzymes, in which an effective amount of the sHSPs are added.

To achieve the above objects, in one aspect, the present invention provides a method for separating and purifying a target protein from a cell in which the target protein is expressed or culture broth thereof, wherein an effective amount of the sHSPs are added in a process for separation and purification to prevent the target protein degradation by proteases.

In another aspect, the present invention provides a method for preparing a target protein by cell cultivation, wherein an effective amount of the sHSPs are added in a cultivation process to prevent target protein degradation by proteases.

In still another aspect, the present invention provides a method for preparing a target protein by cell cultivation, wherein the cell recombined with a sHSP gene is used to prevent target protein degradation by proteases in cultivation processes.

In the present invention, the cell recombined with the sHSP gene is a cell, into a chromosome of which the sHSP gene is inserted, or a cell transformed with recombinant vector containing the sHSP gene, and also, a cell which is recombined so that the sHSP gene and a target protein gene are coexpressed as fusion protein form.

In further another aspect, the present invention provides a method for separating and purifying a target protein from a cell in which the target protein is expressed or culture broth thereof using chromatography, wherein chromatography having an effective amount of sHSPs fixed on resin or bead thereof is used to prevent target protein degradation by proteases.

In yet another aspect, the present invention provides a method for preparing a target material from a substrate by a reaction using a whole cell enzyme or a partially purified enzyme, wherein an effective amount of sHSPs are added in enzyme reaction processes to prevent enzyme degradation by proteases.

In still another aspect, the present invention provides a method wherein the sHSPs are used in a process dealing with target proteins to prevent target protein degradation by proteases.

In the present invention, the sHSPs are preferably one or more selected from the group consisting of IbpA derived from *Agrobacterium tumefaciens*, sHSPs derived from *Arabidopsis thaliana*, HSPB, HSPH, HSPC and HSPF derived from *Bradyrhizobium japonicum*, IbpA derived from *Brucella suis*, sHSPs derived from *Bruchnera aphidicola*, IbpA derived from *Bruchnera aphidicola* (*Acyrthosiphon pisum*), sHSPs derived from *Citrus tristeza* virus, IbpA and IbpB derived form *E. coli*, IbpB derived from *Helicobacter pylori*, HSP27 and α,β-crystallin derived from Human, HSP16.5 derived from *Methanococcus jannaschii*, IbpA derived from *Methanopyrus kandleri*, HSP25 derived from Murine, sHSPs derived from *Mycobacterium leprae*, HSP16.3 derived from *Mycobacterium tuberculosis*, IbpB derived from *Pirellula* sp., HSP18.1 derived from *Pisum sativum* (pea), sHSPs derived from *Plasmodium falciparum*, IbpA derived from the genus *Pseudomonas*, HSP26 derived from *Saccharomyces cerevisiae*, IbpA and IbpB derived from *Salmonella enterica* subsp. *enterica* serovar *Typhi*, IbpA and IbpB derived from *Salmonella typhimurium*, IbpA derived from *Shewanella oneidensis*, IbpA and IbpB derived from *Shigella flexneri*, IbpA derived from *Sinorhizobium meliloti*, IbpA derived from *Streotocuccus pyogenes*, sHSPs derived from *Streptomyces coelicolor*, sHSPs derived from *Sulfolobus solfataricus*, HSP16 derived from *Synechococcus vulcanus*, IbpA derived from *Thermoanaerobacter tengcongensis*, IbpA derived from *Thermoplasma acidophilum*, IbpA and IbpB derived from *Yersinia pestis*, and more perfectly one or more selected from the group consisting of IbpA, IbpB and IbpAB derived from *E. coli* and IbpA derived from the genus *Pseudomonas*, and HSP26 derived from *Saccharomyces cerevisiae*.

In the present invention, the amount of the sHSPs that is added for the prevention of protein degradation by proteases is preferably in a range of 0.1 to 50 parts by weight, and more preferably 0.5 to 20 parts by weight, relative to 100 parts by weight of total protein. If the sHSPs are added at the amount of less than 0.1 part by weight, it is absolutely insufficient for the prevention of protein degradation, and if they are added at the amount of more than 20 parts by weight, an excess of the sHSPs either interferes with the separation and purification of target proteins or causes an adverse effect in view of the cost of the sHSPs.

DETAILED DESCRIPTION OF THE INVENTION

Figure 1:
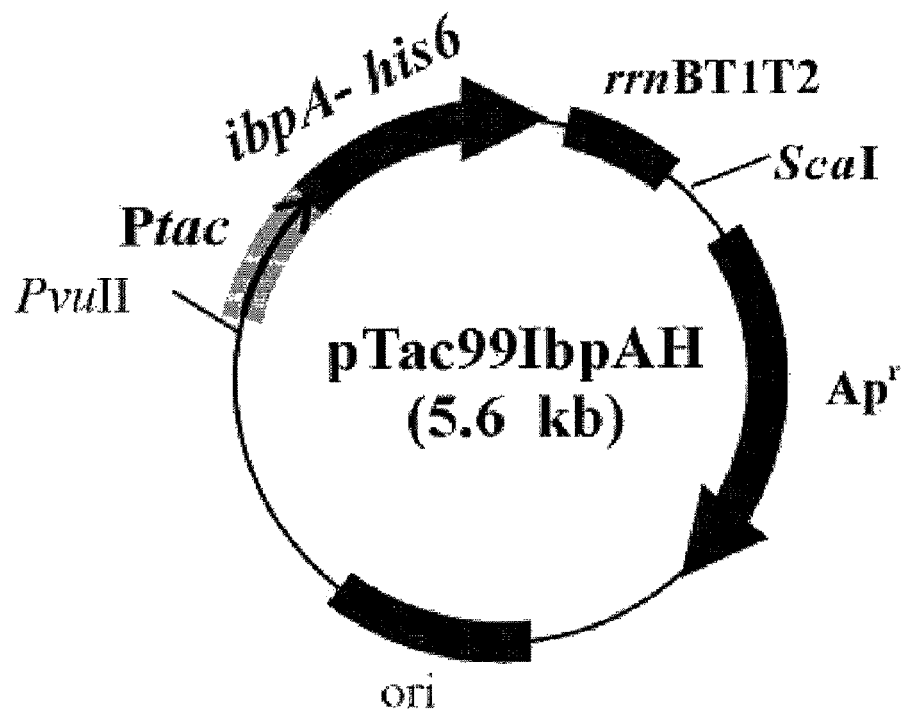
FIG. 1 is a gene map of plasmid pTac99IbpAH.
Figure 2:
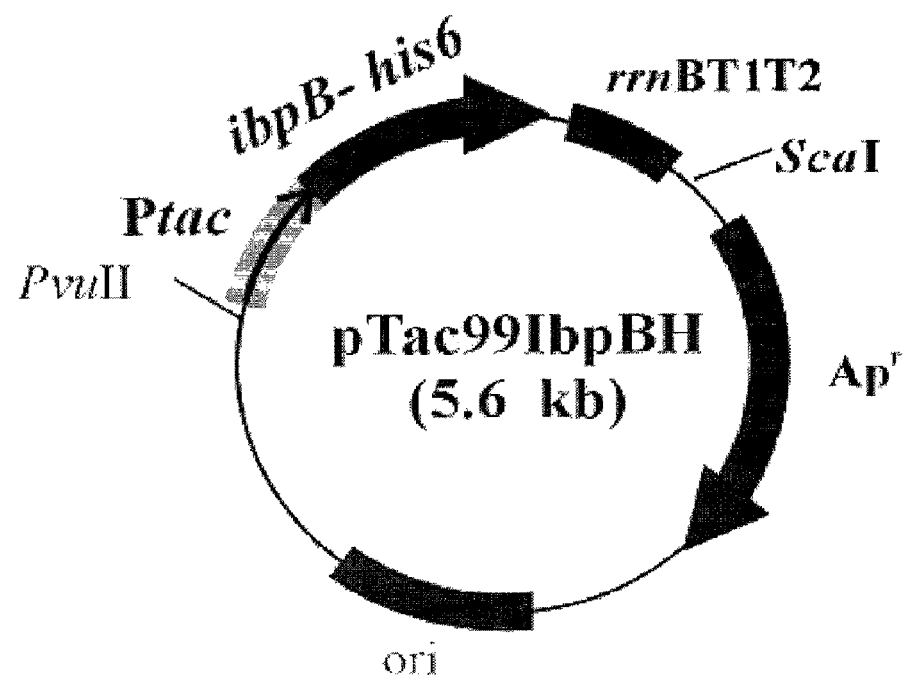
FIG. 2 is a gene map of plasmid pTac99IbpBH.
Figure 3:
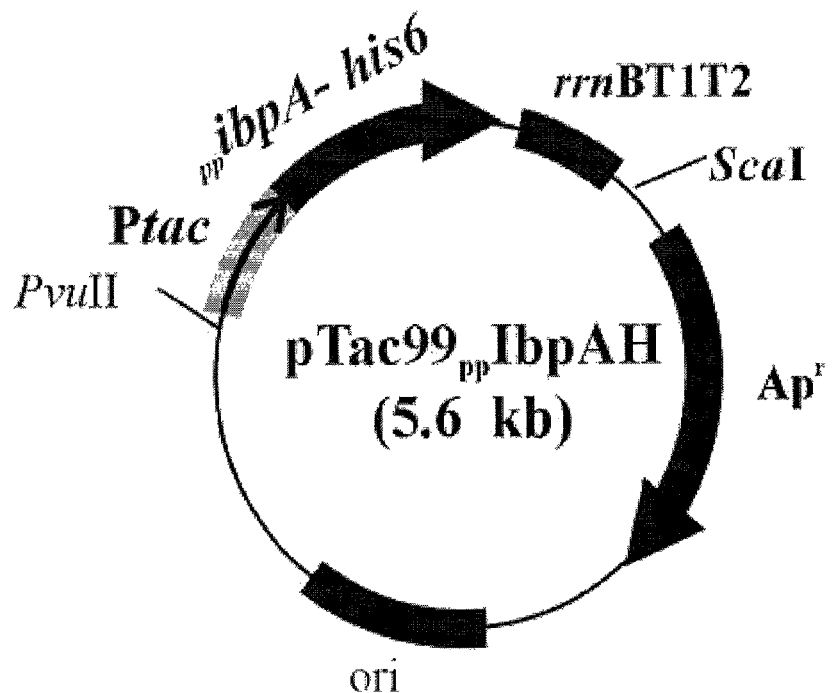
FIG. 3 is a gene map of plasmid pTac99$_{PP}$IbpAH.
Figure 4:
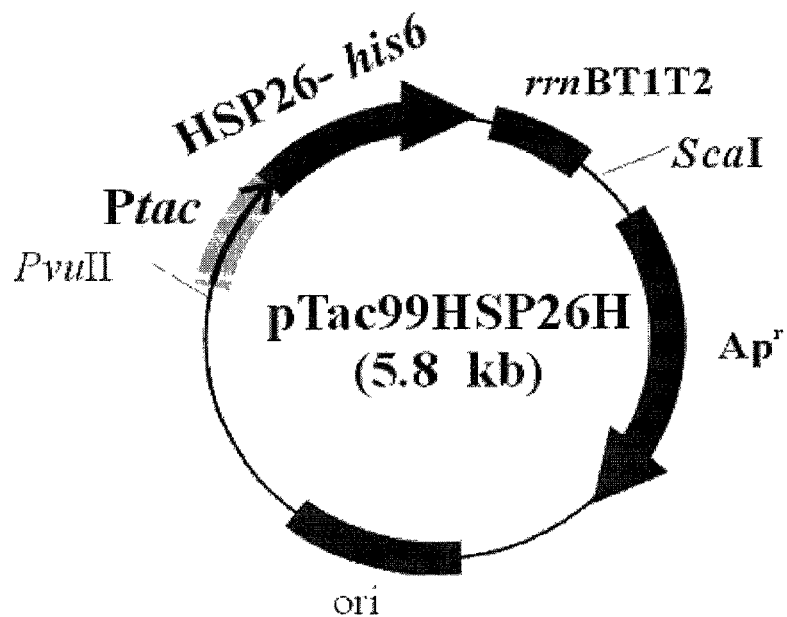
FIG. 4 is a gene map of plasmid pTac99HSP26H.

Hereinafter, the present invention will be described in further detail by examples. It will however be obvious to a person skilled in the art that these examples are provided for illustrative purpose only and are not construed to limit the scope of the present invention.

Particularly, the Examples herein are intended to illustrate IbpA and IbpB derived from *E. coli*, IbpA derived from the genus *Pseudomonas*, and HSP26 derived from *Saccharomyces cerevisiae* as sHSPs, however it should be borne in mind the sHSPs of Table 2 can be used for the present invention without limitation.

Example 1

Preparation of Recombinant Plasmid Containing IbpA, IbpB or HSP26 Gene

Chromosomal DNAs of *E. coli* W3110 (ATCC 39936), *Pseudomonas putida* KT2440 (ATCC 47054) and *Saccharomyces cerevisiae* were isolated and purified according to the method of Sambrook et al. (Molecular Cloning, 2nd ed., Cold Spring Harbor Laboratory Press, NY, 1989).

*E. coli* W3110, *Pseudomonas putida* KT2440 and *Saccharomyces cerevisiae* were cultured in 500 mL LB (Luria-Bertani) medium for 24 hours, respectively. The strains in early exponential growth phase were collected by centrifugation, and then, suspended in 50 mL TE solution (10 mM Tris, 1 mM EDTA; pH 7.6) containing 10 mg/mL lysozyme (Sigma Co., USA). The strain suspensions were cultured at room temperature for 24 hours with slow stirring.

In order to disrupt the strains and remove proteins, the culture broth was added with 16 mL of 10% SDS (sodium dodecyl sulfate) solution and 570 µL of 20 mg/mL Proteinase K (Sigma Co., USA), followed by a reaction at 37° C. for 1 hour.

Next, 14 mL of 5 M NaCl solution and 10.66 mL of 10% CTAB (cetyltrimethyl ammoniumbromide, Sigma Co., USA) dissolved in 0.7 M NaCl solution were added to the reaction solution and then reacted at 65° C. for 10 minutes. After this, chloroform:isoamylalcohol (24:1) of the same volume as the reaction solution was added to the reaction solution and carefully mixed at room temperature for 2 hours. The mixed solution was centrifuged at 6,000 rpm for 10 minutes, and the supernatant was transferred into a beaker, to which cooled ethanol that is two times the volume of the supernatant was added slowly to precipitate chromosomal DNA. The precipitated DNA was wound around a glass rod and taken out. The glass rod was air-dried to remove ethanol, and the chromosomal DNA was dissolved in 1 mL TE solution.

RNase (Sigma Co., USA) was added to the DNA solution to a final concentration of 50 µg/mL, followed by a reaction at 37° C. for 1 hour. After the reaction, chloroform:isoamylalcohol (24:1) of the same volume as the reaction solution was added, and carefully mixed at room temperature for 2 hours.

The mixed solution was centrifuged at 6,000 rpm for 10 minutes, and the supernatant was transferred into a beaker, to which cooled ethanol that is two times the volume of the supernatant was added slowly to precipitate chromosomal DNA. The precipitated DNA was wound around a glass rod and taken out. The glass rod was air-dried to remove ethanol, and finally, the chromosomal DNAs of purified *E. coli* W3110, *Pseudomonas putida* KT2440 and *Saccharomyces cerevisiae* were dissolved in 1 mL TE solution, respectively.

To make the expression and purification of IbpA, IbpB, $_{PP}$IbpA or HSP26 protein easy, the recombinant plasmids, pTac99IbpAH, pTac99IbpBH, pTac99$_{PP}$IbpAH and pTac99HSP26H were constructed as follow.

Using the chromosomal DNA of *E. coli* W3110 as a template, PCR was performed with primers of SEQ ID NOs: 1 and 2, and primers of SEQ ID NOs: 3 and 4 to obtain ibpA-6his and ibpB-6his genes derived from *E. coli*.

Furthermore, using the chromosomal DNA of *Pseudomonas putida* KT2440 as a template, PCR was performed with primers of SEQ ID NOs: 5 and 6 to obtain $_{PP}$ibpA-6his gene derived from *Pseudomonas putida*. In *Pseudomonas putida* KT2440 genome, ibpB gene has not been yet known.

Using the chromosomal DNA of *Saccharomyces cerevisiae* as a template, PCR was performed with primers of SEQ ID NOs: 7 and 8 to obtain HSP26-6his gene derived from *Saccharomyces cerevisiae*.

All PCRs were performed by the following conditions: initial denaturation at 95° C. for 5 minutes; 30 cycles of denaturation at 95° C. for 50 seconds, annealing at 55° C. for 1 minute, and extension at 72° C. for 1 minute and 30 seconds; and final extension at 72° C. for 5 minutes.

Each of the obtained ibpA-6his, ibpB-6his, $_{PP}$ibpA-6his and HSP26-6his genes was inserted into recombinant plasmid pTac99A digested with EcoRI and HindIII to construct plasmids pTac99IbpAH, pTac99IbpBH, pTac99$_{PP}$IbpAH and pTac99HSP26H, respectively (FIG. 1, FIG. 2, FIG. 3 and FIG. 4).

The recombinant plasmid pTac99A is a plasmid which the trc promoter of pTrc99A (Pharmacia Biotech., Uppsala, Sweden) is converted into the tac promoter of pKK223-3 (Pharmacia Biotech., Uppsala, Sweden) and it is constructed by digesting trc promoter of pTrc99A with restriction enzymes PvuII and EcoRI to obtain tac promoter of pKK223-3 and inserting the gene fragment of the tac promoter into pTrc99A digested with the same restriction enzymes.

```
SEQ ID NO. 1:
5'-ggaattcatgcgtaactttgatttatccccg-3'

SEQ ID NO. 2:
5'-cccaagcttttaatggtgatgatggtgatggttgatttcgatacggc
gcgg-3'

SEQ ID NO. 3:
5'-ggaattcatgcgtaacttcgatttatcccactg-3'

SEQ ID NO. 4:
5'-cccaagcttttaatggtgatgatggtgatggctatttaacgcgggac
gttcgct-3'

SEQ ID NO. 5:
5'-ggaattcatgaccatgactactgctttc-3'

SEQ ID NO. 6:
5'-cccaagcttttaatggtgatgatggtgatggttcagcgctggtttt
t-3'

SEQ ID NO. 7:
5'-ggaattcatgtcatttaacagtccatttt-3'

SEQ ID NO. 8:
5'-cccaagcttttaatggtgatgatggtgatggttaccccacgattctt
gaga-3'
```

Example 2

Purification of IbpA, IbpB and HSP26 Proteins

The recombinant *E. coli* XL1-Blue (Stratagene, USA) transformed with recombinant plasmids pTac99IbpAH, pTac99IbpBH, pTac99$_{PP}$IbpAH and pTac99HSP26H, containing the gene encoding IbpA, IbpB or HSP26 protein prepared in the Example 1 was cultured in LB medium (yeast extract 5 g/L, tryptophan 10 g/L, NaCl 10 g/L) containing 50 mg/L ampicillin, respectively.

The expressions of IbpA, IbpB, $_{PP}$IbpA and HSP26 proteins were induced by adding 1 mM IPTG (isopropyl-β-thiogalactoside) when optical density (O.D.) was 0.7 at 600 nm by spectrophotometer. 4 hours after induction, 1 mL of each culture broth was taken and centrifuged at 4° C. and 6,000 rpm for 5 minutes, and then the obtained precipitate was washed one time with 0.5 mL TE solution (10 mM Tris-HCl, 1 mM EDTA; pH 8.0) and centrifuged at 4° C. and 6,000 rpm for 5 minutes to obtain a precipitate. The precipitate was suspended in 0.2 mL equilibrium solution (8 M urea, 100 mM NaH$_2$PO$_4$, 10 mM Tris; pH 8.0), and subjected to ultrasonic disruption and fractionation.

The above suspended solution was centrifuged at 4° C. and 10,000 rpm for 10 minutes, and the supernatant was collected and passed through Ni-NTA spin column (Qiagen, USA) pre-equilibrated with the equilibrium solution. And then, the solution was centrifuged at 2,000 rpm for 2 minutes. 600 μL washing solution (8 M urea, 100 mM NaH$_2$PO$_4$, 10 mM Tris; pH 6.3) was passed through the column two times. 200 μL eluant (8 M urea, 100 mM NaH$_2$PO$_4$, 10 mM Tris; pH 4.5) was inserted into the column to purify IbpA, IbpB and HSP26 proteins.

200 μL of each of the solution containing the purified IbpA, IbpB and HSP26 proteins was taken and mixed with 50 μL of SDS-PAGE sample solution (25% glycerol, 2% SDS, 14.4 mM 2-mercaptoethanol, 0.1% bromophenol blue, 60 mM Tris-HCl). The mixed solution was boiled for 10 minutes and was subjected to SDS-PAGE gel electrophoresis in 12% separating gel. Next, the gel was soaked in a staining solution (methanol 40%, acetic acid 10%, 0.25 g/L Coomassie brilliant blue R) for over 2 hours to be stained and soaked two times in a decolorizing solution (40% methanol, 7% acetic acid) for over 2 hours each time to be decolorized.

Figure 5:
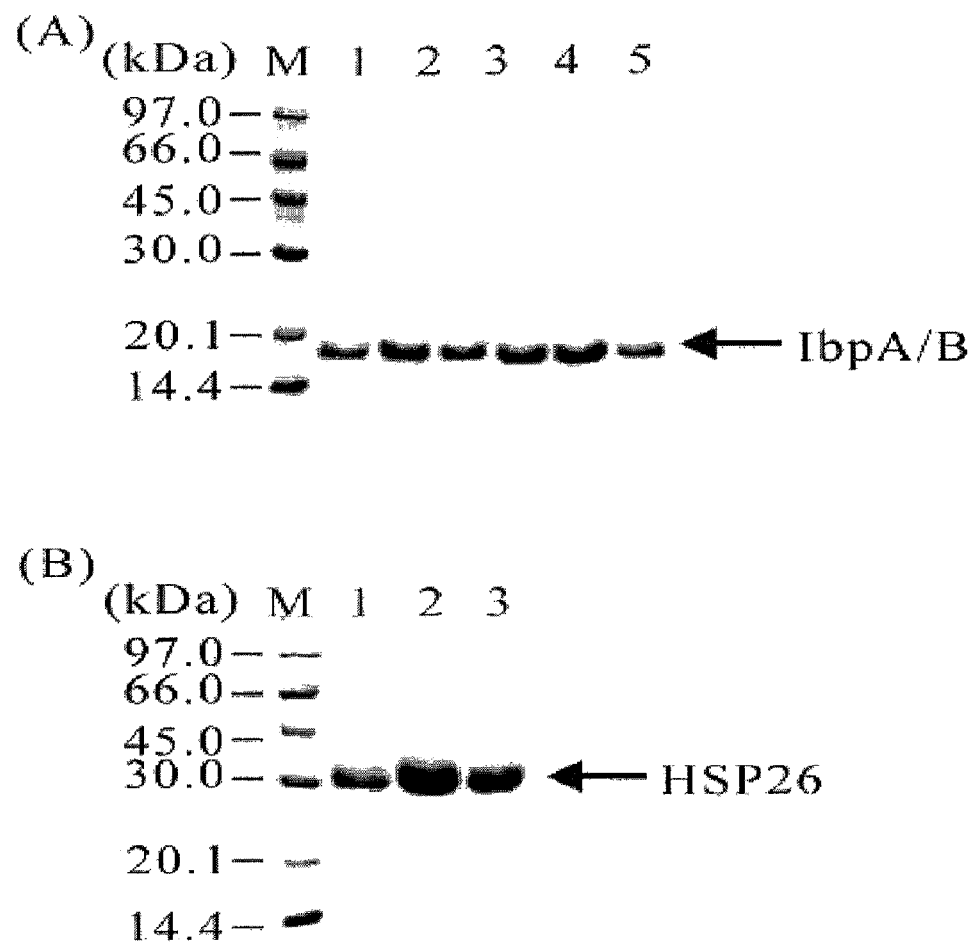
FIG. 5 is an electrophoretic picture showing the result of protein purification of IbpA, IbpB, $_{PP}$IbpA or HSP26 expressed from recombinant *E. coli* XL1-Blue transformed with recombinant plasmid pTac99IbpAH, pTac99IbpBH, pTac99$_{PP}$IbpAH, and pTac99HSP26H, respectively. In (A), lane M shows Molecular mass standard, lanes 1 and 2 show purified IbpA, lanes 3 and 4 show purified IbpB, lanes 5 and 6 show purified $_{PP}$IbpA. In (B), lane M shows Molecular mass standard, lanes 1 to 3 show purified HSP26.

FIG. 5 is an electrophoretic picture showing the result of protein purification of IbpA, IbpB, $_{PP}$IbpA and HSP26 expressed from recombinant *E. coli* XL-1 Blue transformed with recombinant plasmid pTac99IbpAH, pTac99IbpBH, pTac99 $_{PP}$IbpAH and pTac99HSP26H, respectively. As shown in FIG. 5, the purity of the purified IbpA, IbpB, $_{PP}$IbpA and HSP26 proteins was almost 100%.

Example 3

The Effect of sHSPs on Target Protein Degradation by Trypsin

Since target proteins are easily attacked by protease in a lysis solution of cells, the loss of target proteins is serious. In this Example, human serum albumin as a target protein was diluted in a lysis solution, and then cultured with trypsin of varied concentration as protease for 2 hours at room temperature. The concentration of protease was changed to 0, 1/10, 1/20, 1/30 and 1/50 relative to the target protein. IbpA and IbpB derived from *E. coli*, and HSP26 derived from *Saccharomyces cerevisiae* were used as sHSPs.

Figure 6:
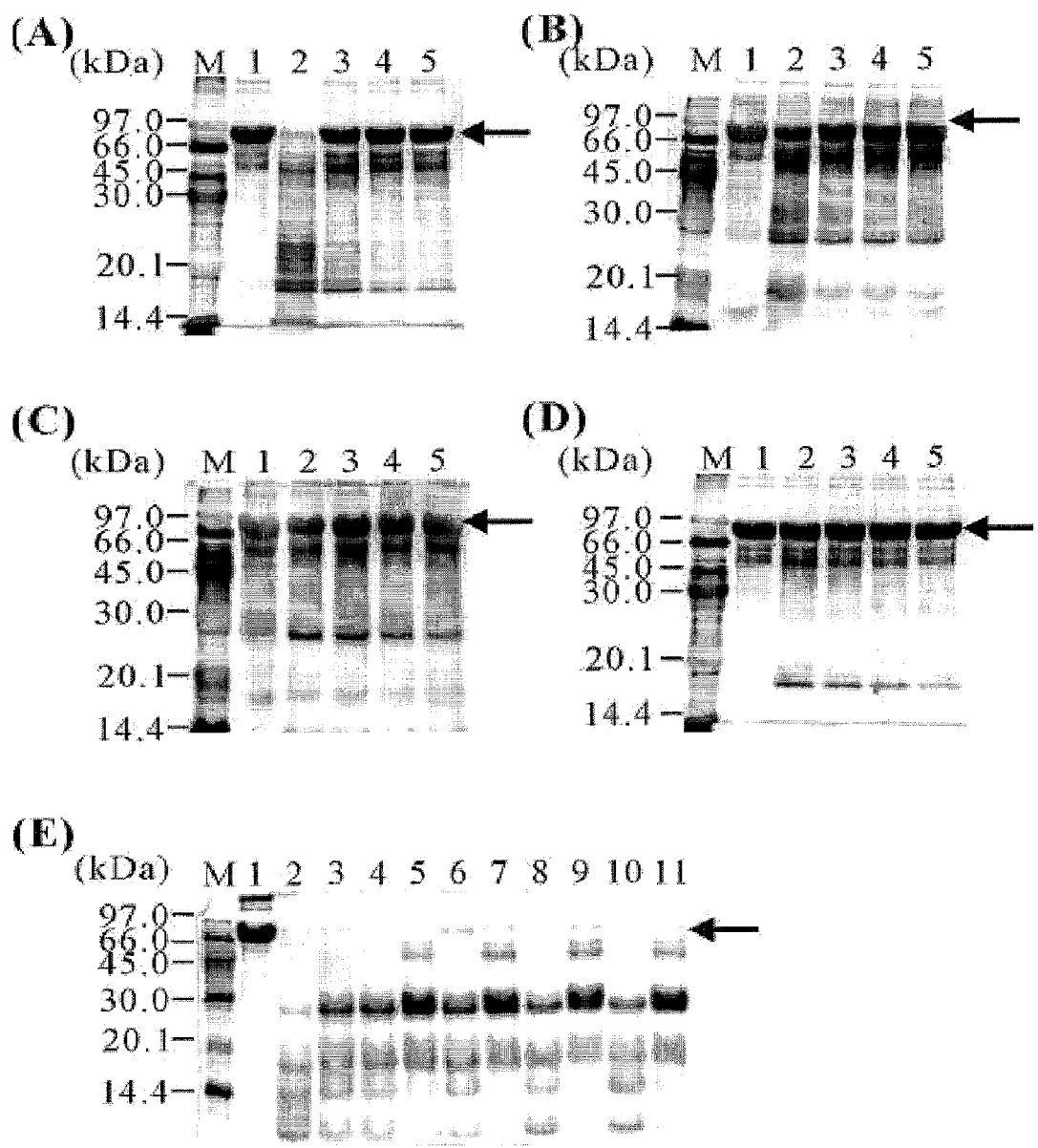
FIG. 6 is an electrophoretic picture showing the effect of protease inhibition by sHSPs in lysis solutions in which human serum albumin is added. (A) represents a lysis solution without sHSPs as a control, lane M shows Molecular mass standard, lane 1 shows a lysis solution with only 0.5 μg/μL human serum albumin added, lane 2 shows a solution in which 0.05 μg/μL trypsin is added to 0.5 μg/μL human serum albumin, lane 3 shows a solution in which 0.025 μg/μL trypsin is added to 0.5 μg/μL human serum albumin, lane 4 shows a solution in which 0.017 μg/μL trypsin is added to 0.5 μg/μL human serum albumin, and lane 5 shows a solution in which 0.01 μg/μL trypsin is added to 0.5 μg/μL human serum albumin. (B), (C) and (D) show lysis solutions in which IbpA, IbpB and HSP26 are added respectively, lane M shows Molecular mass standard, lane 1 shows a lysis solution in which only 0.005 μg/μL sHSPs are added to 0.5 μg/μL human serum albumin, lane 2 shows a solution in which 0.05 μg/μL trypsin and 0.005 μg/μL sHSPs are added to 0.5 μg/μL human serum albumin, lane 3 shows a solution in which 0.025 μg/μL trypsin and 0.005 μg/μL sHSPs are added to 0.5 μg/μL human serum albumin, lane 4 shows a solution in which 0.017 μg/μL trypsin and 0.005 μg/μL sHSPs are added to 0.5 μg/μL human serum albumin, and lane 5 shows a solution in which 0.01 μg/μL trypsin and 0.005 μg/μL sHSPs are added to 0.5 μg/μL human serum albumin. (E) is a lysis solution in which various protease inhibitors are added, lane M shows Molecular mass standard, lane 1 shows a lysis solution in which only 0.5 μg/μL human serum albumin is added, lane 2 shows a solution in which 0.05 μg/μL trypsin is added to 0.5 μg/μL human serum albumin, lane 3 shows a solution in which 0.025 μg/μL trypsin is added to 0.5 μg/μL human serum albumin, lane 4 shows a solution in which 0.05 μg/μL trypsin and 1 mM PMSF are added to 0.5 μg/μL human serum albumin, and lane 5 shows a solution in which 0.025 μg/μL trypsin and 1 mM PMSF are added to 0.5 μg/μL human serum albumin, lane 6 shows a solution in which 0.05 μg/μL trypsin and 4 mM Pefabloc SC are added to 0.5 μg/μL human serum albumin, lane 7 shows a solution in which 0.025 μg/μL trypsin and 4 mM Pefabloc SC are added to 0.5 μg/μL human serum albumin, lane 8 shows a solution in which 0.05 μg/μL trypsin and cocktail inhibitor (7 mL/tablet) are added to 0.5 μg/μL human serum albumin, lane 9 shows a solution in which 0.025 μg/μL trypsin and cocktail inhibitor (7 mL/tablet) are added to 0.5 μg/μL human serum albumin, and lane 10 shows a solution in which 0.05 μg/μL trypsin and 1 mM EDTA are added to 0.5 μg/μL human serum albumin, and lane 11 shows a solution in which 0.025 µg/µL trypsin and 1 mM EDTA are added to 0.5 µg/µL human serum albumin. The arrows represent human serum albumin.

FIG. 6 is an electorphoretic picture showing the effect of protease inhibition by the sHSPs in a lysis solution having human serum albumin added. As shown in FIG. 6, a target protein, human serum albumin was hardly degraded in a solution with sHSPs, on the other hand, in a control, most of the human serum albumins were degraded by an attack of protease. In a comparison of lanes 2 in FIG. 6(A) to 6(D), human serum albumins were completely degraded by trypsin, while it was hardly degraded in a solution with a small amount of sHSP. Also, in a comparison of lanes 2 and 3 in FIG. 6 (B)-6(D), and lanes 4 to 11 in FIG. 6(E), it was confirmed that the sHSPs prevent target protein degradation by protease much more effectively than traditional protease inhibitors do.

Example 4

The Effect of sHSPs on Target Protein Degradation by Proteinase K

In this Example, the same experiment as the above was performed using another protease, Proteinase K. Human serum albumin as a target protein was diluted in a lysis solution, and cultured with Proteinase K of varied concentration for 2 hours at room temperature. The concentration of protease was varied to 0, 1/300, 1/1000, 1/3000 and 1/10000 relative to the target protein. IbpA and IbpB derived from *E. coli*, and HSP26 derived from *Saccharomyces cerevisiae* were used as sHSPs.

Figure 7:
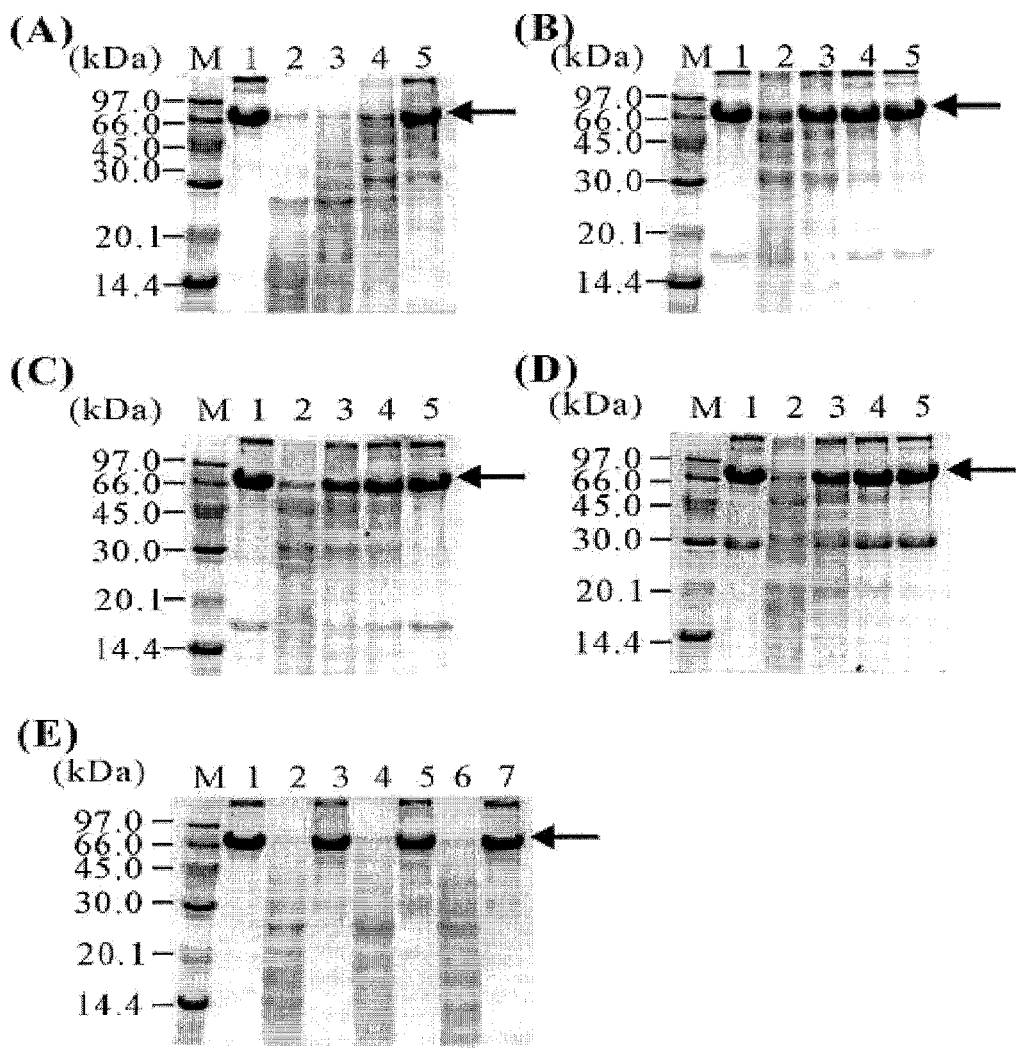
FIG. 7 is an electrophoretic picture showing the effect of protease inhibition by sHSPs in lysis solutions in which human serum albumin is added. (A) represents a lysis solution without sHSPs as a control, lane M shows Molecular mass standard, lane 1 shows a lysis solution in which only 0.5 µg/µL human serum albumin is added, lane 2 shows a solution in which $1.5 \times 10^{-3}$ µg/µL Proteinase K is added to 0.5 µg/µL human serum albumin, lane 3 shows a solution in which $0.5 \times 10^{-3}$ µg/µL Proteinase K is added to 0.5 µg/µL human serum albumin, lane 4 shows a solution in which $1.5 \times 10^{-4}$ µg/µL Proteinase K is added to 0.5 µg/µL human serum albumin, and lane 5 shows a solution in which $0.5 \times 10^{-4}$ µg/µL Proteinase K is added to 0.5 µg/µL human serum albumin. (B), (C) and (D) represent lysis solutions in which IbpA, IbpB and HSP26 are added, respectively, lane M shows Molecular mass standard, lane 1 shows a lysis solution having only 0.005 µg/µL sHSPs added to 0.5 µg/µL human serum albumin, lane 2 shows a solution having $1.5 \times 10^{-3}$ µg/µL Proteinase K and 0.005 µg/µL sHSPs added to 0.5 µg/µL human serum albumin, lane 3 shows a solution having $0.5 \times 10^{-3}$ µg/µL Proteinase K and 0.005 µg/µL sHSPs added to 0.5 µg/µL human serum albumin, lane 4 shows a solution having $1.5 \times 10^{-4}$ µg/µL Proteinase K and 0.005 µg/µL sHSPs added to 0.5 µg/µL human serum albumin, and lane 5 shows a solution having $0.5 \times 10^{-4}$ µg/µL Proteinase K and 0.005 µg/µL sHSPs added to 0.5 µg/µL human serum albumin. The arrows represent human serum albumin. (E) represents a lysis solution having various protease inhibitors added, lane M shows Molecular mass standard, lane 1 shows a solution having only 0.5 µg/µL human serum albumin added, lane 2 shows a solution having $0.5 \times 10^{-3}$ µg/µL Proteinase K and 4 mM Pefabloc SC added to 0.5 µg/µL human serum albumin, lane 3 shows a solution having $1.5 \times 10^{-4}$ µg/µL Proteinase K and 4 mM Pefabloc SC added to 0.5 µg/µL human serum albumin, lane 4 shows a solution having $0.5 \times 10^{-3}$ µg/µL Proteinase K and cocktail inhibitor (7 mL/tablet) added to 0.5 µg/µL human serum albumin, lane 5 shows a solution having $1.5 \times 10^{-4}$ µg/µL Proteinase K and cocktail inhibitor (7 mL/tablet) added to 0.5 µg/µL human serum albumin, lane 6 shows a solution having $0.5 \times 10^{-3}$ µg/µL Proteinase K and 1 mM EDTA added to 0.5 µg/µL human serum albumin, and lane 7 shows a solution having $1.5 \times 10^{-4}$ µg/µL Proteinase K and 1 mM EDTA added to 0.5 µg/µL human serum albumin. The arrows represent human serum albumin.

FIG. 7 is an electorphoretic picture showing the effect of protease inhibition by sHSPs in a lysis solution having human serum albumin added. As shown in FIG. 7, a target protein, human serum albumin was hardly degraded in a solution with sHSPs, on the other hand, in a control, most of the human serum albumins were degraded by an attack of protease. In a comparison of lanes 3 and 4 in FIG. 7(A) to 7(D), respectively, most of the human serum albumins were degraded by Proteinase K, while it was hardly degraded in a solution with small amount of sHSP.

Also, in a comparison of lanes 3 in FIG. 7(B)-7(D), and lanes 2, 4 and 6 in FIG. 7(E), it was confirmed that the sHSPs prevent target protein degradation by protease much more effectively than traditional protease inhibitors do.

Indirect Example

In the above Examples, it is illustrated that the sHSPs prevent target protein degradation by protease when the sHSPs were added in a process for separating and purifying target proteins. However, in view of the fact that protease is produced and released when most of the microorganisms are cultured, it will be obvious to a person skilled in the art that the target protein degradation by protease can be prevented even when the sHSPs are added in a cultivation process for preparing a target protein, or when sHSPs and a target protein are simultaneously coexpressed by transforming a cell for preparing a target protein with sHSP gene, and then culturing.

Figure 8:
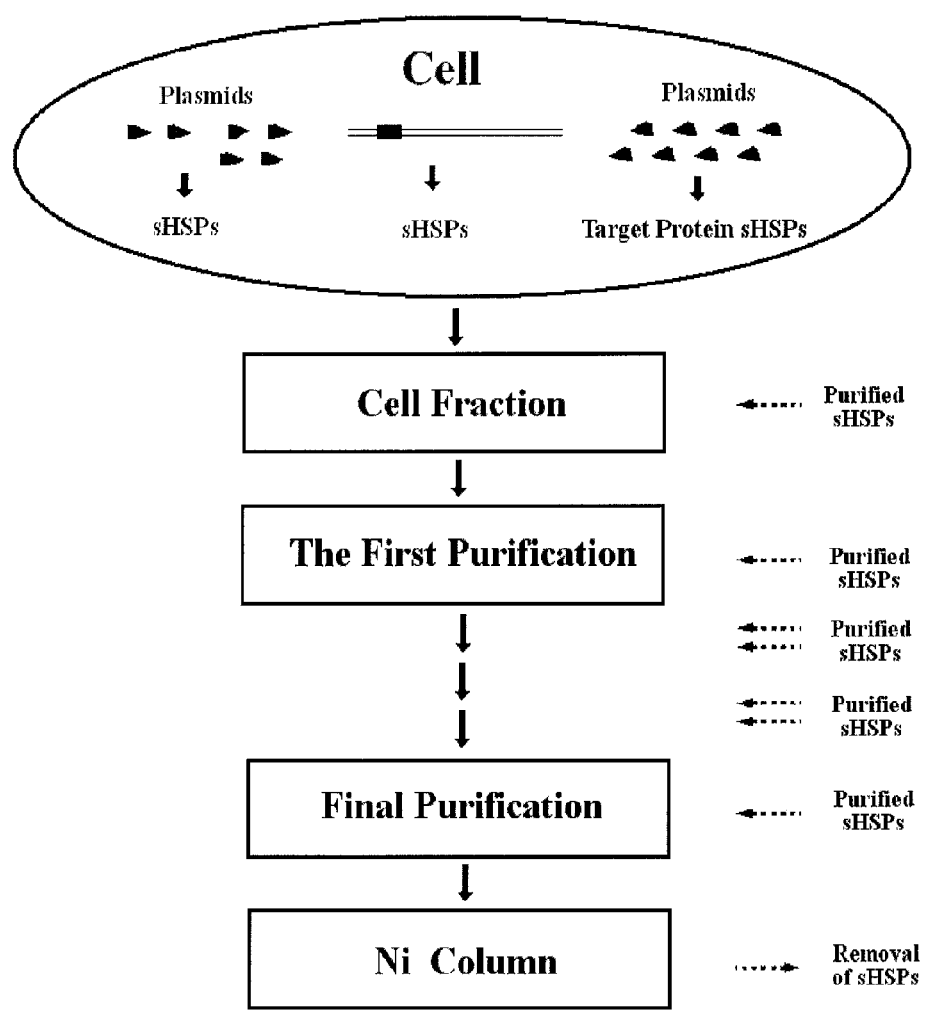
FIG. 8 is a schematic diagram on the prevention of target protein degradation by sHSPs in an isolation and purification process.

Accordingly, the present invention showed a schematic diagram in the FIG. 8 to minimize target protein degradation in a process for isolating and purifying organisms. As shown in the FIG. 8, it includes a method in which the purified sHSPs are added in each step of the process for separation and purification of a target protein, or a method in which the sHSPs are coexpressed with a target protein in vivo in initial step. When the sHSPs are coexpressed with a target protein in a cell, the sHSPs can be expressed by inserting into chromosome of a cell, or inserting in a form of a plasmid, or by preparing in a form of fusion protein with a target protein using a direct linker peptide.

Also, it will be obvious to those skilled in the art that the target protein degradation by protease can be prevented when the sHSPs are added in a reaction process using a whole cell enzyme or a partially purified enzyme, since the whole cell enzyme or the partially purified enzyme contains a protease.

While the present invention has been described with reference to the particular illustrative embodiment, it is not to be restricted by the embodiment but only by the appended claims. Accordingly, it is to be appreciated that those skilled in the art can change or modify the embodiment without departing from the scope and spirit of the present invention.

INDUSTRIAL APPLICABILITY

As described above in detail, the present invention has the effect of providing a method for preventing target protein degradation by protease, in which sHSPs are used in cultivation, separation and purification processes for preparing a target protein, and an enzyme reaction process using the target protein as a biocatalyst. By a process for separation and purification of an organism using the sHSPs, such as IbpA, IbpB, IbpAB, HSP26 according to the present invention, the loss of target proteins by protease can be prevented, and the sHSPs prevent target protein degradation by protease much more efficiently than the expensive traditional protease inhibitors do. Therefore, the present invention is expected to be useful in improving methods for preparing and employing target proteins effectively.

---

What is claimed is:

1. A method for separating and purifying a target protein from a cell, in which the target protein is expressed, or a culture broth thereof, wherein sHSPs are added in a process for separation and purification in an amount effective to prevent degradation of the target protein by proteases and wherein the sHSPs are one or more selected from the group consisting of IbpA derived from *Agrobacterium tumefaciens*, sHSPs derived from *Arabidopsis thaliana*, HSPB HSPH HSPC and HSPF derived from *Bradyrbizobium japonicum*, IbpA derived from *Brucella suis*, sHSPs derived from *Bruchnera aphidicola*, IbpA derived from *Bruchnera aphidicola* (*Acyrthosiphon pisum*), sHSPs derived from *Citrus tristeza* virus, IbpA and IbpB derived from *E. coli*, IbpB derived from

*Helicobacter pylori*, HSP27 and α,β-crystallin derived from Human, HSP16.5 derived from *Methanococcus jannaschii*, IbpA derived from *Methanopyrus kandleri*, HSP25 derived from Murine, sHSPs derived from *Mycobacterium leprae*, HSP16.3 derived from *Mycobacterium tuberculosis*, IbpB derived from *Pirellula* sp., HSP18.1 derived from *Pisum sativum* (pea), sHSPs derived from *Plasmodium falciparum*, IbpA derived from the genus *Pseudomonas*, HSP26 derived from *Saccharomyces cerevisiae*, IbpA and IbpB derived from *Salmonella enterica* subsp. *enterica serovar Typhi*, IbpA and IbpB derived from *Salmonella typhimurium*, IbpA derived from *Shewanella oneidensis*, IbpA and IbpB derived from *Shigella flexneri*, IbpA derived from *Sinorhizobium meliloti*, IbpA derived from *Streotocuccus pyogenes*, sHSPs derived from *Streptomyces coelicolor*, sHSPs derived from *Sulfolobus solfataricus*, HSP16 derived from *Synechococcus vulcanus*, IbpA derived from *Thermoanaerobacter tengcongensis*, IbpA derived from *Thermoplasma acidophilum*, and IbpA and IbpB derived from *Yersinia pestis*.

2. The method for separating and purifying a target protein according to claim 1, wherein the sHSPs are one or more selected from the group consisting of IbpA,
  IbpB and IbpAB derived from *E. coli*, IbpA derived from the genus *Pseudomonas*, and HSP26 derived from *Saccharomyces cerevisiae*.

3. A method for preparing a target protein by cell cultivation, wherein sHSPs are added in a cultivation process in an amount effective to prevent target protein degradation by proteases and wherein the sHSPs are one or more selected from the group consisting of IbpA derived from *Agrobacterium tumefaciens*, sHSPs derived from *Arabidopsis thaliana* HSPB HSPH HSPC and HSPF derived from *Bradyrbizobium japonicum*, IbpA derived from *Brucella suis*, sHSPs derived from *Bruchnera aphidicola*, IbpA derived from *Bruchnera aphidicola* (*Acyrthosiphon pisum*), sHSPs derived from *Citrus tristeza* virus, IbpA and IbpB derived from *E. coli*, IbpB derived from *Helicobacter pylori*, HSP27 and α,β-crystallin derived from Human, HSP16.5 derived from *Methanococcus jannaschii*, IbpA derived from *Methanopyrus kandleri*, HSP25 derived from Murine, sHSPs derived from *Mycobacterium leprae*, HSP16.3 derived from *Mycobacterium tuberculosis*, IbpB derived from *Pirellula* sp., HSP18.1 derived from *Pisum sativum* (pea), sHSPs derived from *Plasmodium falciparum*, IbpA derived from the genus *Pseudomonas*, HSP26 derived from *Saccharomyces cerevisiae*, IbpA and IbpB derived from *Salmonella enterica* subsp. *enterica serovar Typhi*, IbpA and IbpB derived from *Salmonella typhimurium*, IbpA derived from *Shewanella oneidensis*, IbpA and IbpB derived from *Shigella flexneri*, IbpA derived from *Sinorhizobium meliloti*, IbpA derived from *Streotocuccus pyogenes*, sHSPs derived from *Streptomyces coelicolor*, sHSPs derived from *Sulfolobus solfataricus*, HSP16 derived from *Synechococcus vulcanus*, IbpA derived from *Thermoanaerobacter tengcongensis*, IbpA derived from *Thermoplasma acidophilum*, and IbpA and IbpB derived from *Yersinia pestis*.

4. The method for preparing a target protein according to claim 3, wherein the sHSPs are one or more selected from the group consisting of IbpA, IbpB and IbpAB derived from *E. coli*, IbpA derived from the genus *Pseudomonas*, and HSP26 derived from *Saccharomyces cerevisiae*.

\* \* \* \* \*

UNITED STATES PATENT AND TRADEMARK OFFICE
CERTIFICATE OF CORRECTION

PATENT NO. : 8,067,552 B2
APPLICATION NO. : 11/915314
DATED : November 29, 2011
INVENTOR(S) : Sang Yup Lee It is certified that error appears in the above-identified patent and that said Letters Patent is hereby corrected as shown below:

Column 5, line 51: "*Streotocuccus*" should be -- *Streptococcus* --.

Column 15, line 14: "*Streotocuccus*" should be -- *Streptococcus* --.

Column 16, line 19: "*Streotocuccus*" should be -- *Streptococcus* --.

Signed and Sealed this
Twenty-fourth Day of April, 2012

David J. Kappos
*Director of the United States Patent and Trademark Office*

SEQUENCE LISTING

<160> NUMBER OF SEQ ID NOS: 8

<210> SEQ ID NO 1
<211> LENGTH: 31
<212> TYPE: DNA
<213> ORGANISM: Artificial
<220> FEATURE:
<223> OTHER INFORMATION: Primer

<400> SEQUENCE: 1
ggaattcatg cgtaactttg atttatcccc g                          31

<210> SEQ ID NO 2
<211> LENGTH: 51
<212> TYPE: DNA
<213> ORGANISM: Artificial
<220> FEATURE:
<223> OTHER INFORMATION: Primer

<400> SEQUENCE: 2
cccaagcttt taatggtgat gatggtgatg gttgatttcg atacggcgcg g     51

```
<210> SEQ ID NO 3
<211> LENGTH: 34
<212> TYPE: DNA
<213> ORGANISM: Artificial
<220> FEATURE:
<223> OTHER INFORMATION: Primer

<400> SEQUENCE: 3
ggaattcatg cgtaacttcg atttatcccc actg                              34

<210> SEQ ID NO 4
<211> LENGTH: 54
<212> TYPE: DNA
<213> ORGANISM: Artificial
<220> FEATURE:
<223> OTHER INFORMATION: Primer

<400> SEQUENCE: 4
cccaagcttt taatggtgat gatggtgatg gctatttaac gcgggacgtt cgct        54

<210> SEQ ID NO 5
<211> LENGTH: 28
<212> TYPE: DNA
<213> ORGANISM: Artificial
<220> FEATURE:
<223> OTHER INFORMATION: Primer

<400> SEQUENCE: 5
ggaattcatg accatgacta ctgctttc                                     28

<210> SEQ ID NO 6
<211> LENGTH: 47
<212> TYPE: DNA
<213> ORGANISM: Artificial
<220> FEATURE:
<223> OTHER INFORMATION: Primer

<400> SEQUENCE: 6
cccaagcttt taatggtgat gatggtgatg gttcagcgct ggttttt                47

<210> SEQ ID NO 7
<211> LENGTH: 29
<212> TYPE: DNA
<213> ORGANISM: Artificial
<220> FEATURE:
<223> OTHER INFORMATION: Primer

<400> SEQUENCE: 7
ggaattcatg tcatttaaca gtccatttt                                    29

<210> SEQ ID NO 8
<211> LENGTH: 51
<212> TYPE: DNA
<213> ORGANISM: Artificial
<220> FEATURE:
<223> OTHER INFORMATION: Primer

<400> SEQUENCE: 8
cccaagcttt taatggtgat gatggtgatg gttacccccac gattcttgag a          51
```